(12) United States Patent
Mohammadi

(10) Patent No.: US 6,217,913 B1
(45) Date of Patent: Apr. 17, 2001

(54) COSMETIC COMPOSITIONS WITH GORGONIAN EXTRACT

(76) Inventor: Fatemeh Mohammadi, 717 East St., Hebron, CT (US) 06248

(*) Notice: Subject to any disclaimer, the term of this patent is extended or adjusted under 35 U.S.C. 154(b) by 0 days.

(21) Appl. No.: 09/436,116

(22) Filed: Nov. 8, 1999

Related U.S. Application Data

(60) Provisional application No. 60/144,012, filed on Jul. 15, 1999.

(51) Int. Cl.$^7$ .......................... A61K 35/12; A61K 31/74; A61K 6/00; A61K 7/00
(52) U.S. Cl. .................. 424/520; 424/78.02; 424/57; 424/401; 514/887
(58) Field of Search ................ 424/520, 78.02, 424/57, 401; 514/887

(56) References Cited

U.S. PATENT DOCUMENTS

| | | | | |
|---|---|---|---|---|
| 4,139,485 | * | 2/1979 | Imokawa et al. | 510/236 |
| 4,745,104 | | 5/1988 | Jacobs et al. | |
| 4,849,410 | | 7/1989 | Jacobs et al. | |
| 5,015,471 | * | 5/1991 | Birtwistle et al. | 424/70.19 |
| 5,811,114 | * | 9/1998 | Knight et al. | 424/408 |
| 5,849,314 | * | 12/1998 | Dobkowski et al. | 424/401 |
| 5,854,336 | * | 12/1998 | Divone, Sr. et al. | 524/588 |
| 5,939,082 | * | 8/1999 | Oblong et al. | 424/401 |
| 5,968,528 | * | 10/1999 | Deckner et al. | 424/401 |
| 5,972,359 | * | 10/1999 | Sine et al. | 424/401 |
| 6,001,377 | * | 12/1999 | SaNogueira, Jr. et al. | 424/401 |
| 6,039,935 | * | 3/2000 | Mohammadi | 424/59 |
| 6,042,815 | * | 3/2000 | Kellner et al. | 424/63 |

OTHER PUBLICATIONS

Lipo Chemicals Inc. Data Sheet—Apr. 27, 1998, 2 pgs.
J. Org. Chem. 1986, 51, pp. 5140–5143, The Pseudoterosins: A New Class of Antiinflammatory and Analgesic Diterpene Pentosides from the Marine Sea Whip *Pseudopterogorgia elisabethae* (Octocorallia)—by Sally A. Look. William Fenical, Gayle K. Matsumoto and Joh Clardy.
Copy Prescriptives Eye Specialist Visible Action Gel Total Skincare for Eyes box.
Copy of Estee Lauder Diminish Retinol Treatment box.
Proc. Natl. Acad. Sci., USA, vol. 83, pp. 6238–6240, Sep. 1986 "The pseudopterosins: Anti–inflammatory and analgesic natural products from the sea whip *Pseudopterogorgia elisabethae*"—by Sally A. Look, William Fenical, Robert S. Jacobs and Jon Clardy.

\* cited by examiner

*Primary Examiner*—Christopher R. Tate
(74) *Attorney, Agent, or Firm*—Milton L. Honig

(57) ABSTRACT

Cosmetic compositions are provided which include a gorgonian extract, a crosslinked polysiloxane elastomer, a surfactant which is preferably anionic and a pharmaceutically acceptable carrier. Gorgonian extract in the polysiloxane elastomer base mediates redness induced by surfactants leaving the skin also free of itchiness and leaving the skin with a healthy and radiant look.

5 Claims, No Drawings

US 6,217,913 B1

COSMETIC COMPOSITIONS WITH GORGONIAN EXTRACT

This application claims benefit of Provisional No. 60/144,012, filed Jul. 15, 1999.

BACKGROUND OF THE INVENTION

1. Field of the Invention

The invention concerns cosmetic compositions using natural extracts to ameliorate the skin irritating effects of surfactants.

2. The Related Art

Surfactants are known to remove skin protecting lipids. Through this process of removing the skin's protective oils, irritation and even erythema arise in the epidermis. Even the mildest surfactants have some negative irritating effects.

A classic approach to solving this problem is use of only the mildest surfactants. A complementary tactic is the avoidance of solvent vehicles which might enhance the harshness of any surfactant. Control of pH is another factor. Inclusion of additives effective as anti-irritant agents is yet another tactic. Anti-irritant agents are particularly well known in cosmetics incorporating retinoids and/or alpha-hydroxycarboxylic acids.

For instance, U.S. Pat. No. 5,393,526 (Castro et al.) discloses the use of rosmarrinic acid (i.e. rosemary extract) as an anti-irritant to ameliorate the effects of alpha-hydroxy acids. Other similarly effective natural substances include silver birch extract, licorice extract and borage seed oil. None have been specifically indicated as effective against the destructive action of surfactants.

Accordingly, it is an object of the present invention to provide a cosmetic composition formulated with a natural extract for ameliorating any harsh skin properties brought on by the presence of surfactants.

Another object of the present invention is to provide a method for reducing the irritant effects of surfactants in cosmetic compositions.

These and other objects of the present invention will become more readily apparent from consideration of the following summary and detailed description.

SUMMARY OF THE INVENTION

A cosmetic composition is provided which includes:

(i) from about 0.1 to about 35% by weight of a surfactant;
(ii) from about 0.00001 to about 3% of gorgonian extract;
(iii) from about 0.01 to about 30% of a crosslinked non-emulsifying siloxane elastomer; and
(iv) a pharmaceutically acceptable carrier to deliver the surfactant and extract.

DETAILED DESCRIPTION OF THE INVENTION

Now it has been found that gorgonian extract in a crosslinked silicone elastomer base can improve the mildness of surfactant containing cosmetic compositions.

Gorgonian extract is available from the Lipo Chemical Company, Patterson, N.J. as a liquid extract of Sea Whip, *pseudopterogorgia elisabethae*, supplied as a 4% Sea Whip extact in butylene glycol. The Caribbean Sea Whip *pseudoptemgorgia elisabethae* has been reported in Proc. Natl. Acad. Sci. USA, Vol. 83, pp. 6238–6240 (September 1986) as containing pseudoterosins which are diterpene-pentose glycosides. The substances possess anti-inflammatory and analgesic properties. U.S. Pat. No. 4,849,410 and U.S. Pat. No. 4,745,104, both to Jacobs et al., provide further disclosure on the Caribbean gorgonians, and especially pseudopterosin A noting the anti-inflammatory, anti-proliferative and analgesic activities of these materials.

Amounts of gorgonian extract for purposes of this invention will range from about 0.00001 to about 3%, preferably from about 0.0001 to about 1%, more preferably from about 0.001 to about 0.5%, optimally from about 0.01 to about 0.1% by weight.

Crosslinked non-emulsifying siloxane elastomers are a further element of the present invention. These will have an average number of molecular weight in excess of 2,000, preferably in excess of 1 million and optimally it will range from 10,000 to 20 million. The term "non-emulsifying" defines a siloxane from which polyoxyalkylene units are absent. Advantageously, the elastomers are formed from a divinyl compound, particularly a polymer with at least two free vinyl groups, reacting with Si-H linkages of a polysiloxane backbone such as a molecularly spherical MQ resin. Elastomer compositions are commercially available from Dow Coming Company under the product designation DC 9040 and from the General Electric Company under product designation General Electric Silicone 1229 with CTFA name of Cyclomethicone and Dimethicone/Vinyl Dimethicone Cross Polymer, delivered as 20–35% elastomer in a cyclomethicone carrier. Amounts of the elastomer may range from about 0.01 to about 30%, preferably from about 0.5 to about 10%, optimally from about 1 to about 5% by weight.

Surfactants will be a component of compositions according to the present invention. The surfactant may be one selected from the group consisting of anionic, cationic, amphoteric and zwitterionic actives as well as combinations thereof. Amounts of the surfactant may range from about 0.1 to about 35%, preferably from about 0.3 to about 20%, more preferably from about 0.3 to about 10%, optimally from about 0.5 to about 5% by weight.

Thus, as examples of anionic surfactants which can be used, by themselves or in mixtures, within the framework of the present invention, are the salts, in particular alkali metal (e.g. sodium and potassium), ammonium, alkanolammonium, and alkaline earth (e.g. magnesium and calcium) salts, of the following compounds: alkylsulphates, alkyl-ether-sulphates, alkylamido-ether-sulphates, monoglyceride-sulphates, alkylglycerylsulphonates, alkylsulphonates, alkylphosphates, alkylamidosulphonates, alkylarylsulphonates, alpha-olefin-sulphonates, alkylsulphosuccinates, alkyl-ether-sulpho-succinates, alkylamidosulphosuccinates, alkylsulphosuccinates, alkylsulphoacetates, alkyl-ether-phosphates, acylisethionates, and N-acylamino acids such as N-acylsarcosinates, N-acylglutamates and N-acyllaurates. Among other anionic surfactants generally referred to as soaps are the salts of oleic, ricinoleic, palmitic, myristic, lauric and stearic acids. It is also possible to use weakly anionic surfactants such as salts of acyllactylates.

Amphoteric or zwitterionic surfactants which may preferably be used in accordance with the present invention are secondary or tertiary aliphatic amine derivatives in which the aliphatic radical is a linear or branched chain containing from 8 to 22 carbon atoms and containing at least one water-solubilizing anionic group, for example, carboxylate, sulphonate, sulphate, phosphate or phosphonate. There may be mentioned alkylbetaines, alkyldimethylbetaines, alkylsulphobetaines, alkylamidoalkylbetaines, alkylamidoalkylsulphobaines, and imidazoline derivatives such as amphocarboxyglycinate or amphocarboxypropionate derivatives.

Cosmetic compositions of the present invention may contain substantial levels of water, preferably as part of an emulsion. Amounts of water may range from about 10 to about 95%, preferably from about 25 to about 80%, optimally from about 35% to about 65% by weight. Emulsions may be of the oil-in-water, water-in-oil or duplex variety. Aqueous to oily phases may range in weight from about 10:1 to about 1:10, preferably from about 1:1 to about 2:1, optimally from about 1:1 to about 1.5:1.

Compositions of the invention may optionally contain a skin conditioning agent. The agents may be selected from humectants, exfoliants or emollients.

Humectants are polyhydric alcohols intended for moisturizing, reducing scaling and stimulating removal of built-up scale from the skin. Typical polyhydric alcohols include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Most preferably the humectant is glycerin. Amounts of humectant may range anywhere from about 1 to about 50%, preferably from about 10 to about 40%, optimally from about 25 to about 35% by weight.

Exfoliants according to the present invention may be selected from alpha-hydroxycarboxylic acids, beta-hydroxycarboxylic acids and salts of these acids. Most preferred are glycolic, lactic and salicylic adds and their ammonium or alkali metal salts. Amounts may range from about 0.01 to about 15%, preferably from about 0.5 to about 10%, optimally from about 1 to about 8% by weight.

When the conditioning agent is an emollient it may be selected from hydrocarbons, fatty acids, fatty alcohols and esters. Petrolatum is the most preferred hydrocarbon type of emollient conditioning agent. Other hydrocarbons that may be employed include mineral oil, polyolefins such as polydecene, and paraffins such as isohexadecane (e.g. Permethyl 99® and Permethyl 101®).

Fatty adds and alcohols will have from 10 to 30 carbon atoms. Illustrative of this category are pelargonic, lauric, myristic, palmitic, stearic, isostearic, hydroxystearic, oleic, linoleic, ricinoleic, arachidic, behenic and erucic acids and their alcohol forms.

Oily ester emollients may be those selected from one or more of the following classes:

1. Triglyceride esters such as vegetable and animal fats and oils. Examples include castor oil, cocoa butter, safflower oil, cottonseed oil, corn oil, olive oil, cod liver oil, almond oil, avocado oil, palm oil, sesame oil, squalane, Kikui oil, maleated soybean oil and soybean oil.

2. Acetoglyceride esters, such as acetylated monoglycerides.

3. Ethoxylated glycerides, such as ethoxylated glyceryl monostearate.

4. Alkyl esters of fatty adds having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

5. Alkenyl esters of fatty acids having 10 to 20 carbon atoms. Examples thereof include oleyl myristate, oleyl stearate, and oleyl oleate.

6. Ether-esters such as fatty add esters of ethoxylated fatty alcohols.

7. Polyhydric alcohol esters. Ethylene glycol mono and di-fatty acid esters, diethylene glycol mono- and di-fatty add esters, polyethylene glycol (200–6000) mono- and di-fatty acid esters, polypropylene glycol 2000 monooleate, polypropylene glycol 2000 monostearate, ethoxylated propylene glycol monostearate, glyceryl mono- and di-fatty add esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty add esters, and polyoxyethylene sorbitan fatty acid esters are satisfactory polyhydric alcohol esters.

8. Wax esters such as beeswax, spermaceti, myristyl myristate, stearyl stearate.

Amounts of the emollient may range from about 1 to about 50%, preferably from about 3 to about 25%, optimally from about 5 to about 20% by weight.

Preservatives can desirably be incorporated into the compositions of this invention to protect against the growth of potentially harmful microorganisms. While it is in the aqueous phase that microorganisms tend to grow, microorganisms can also reside in the oil phase. As such, preservatives which have solubility in both water and oil are preferably employed in the present compositions. Suitable traditional preservatives are alkyl esters of parahydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methyl paraben, propyl paraben, butyl paraben, imidazolidinyl urea, sodium dehydroacetate and benzyl alcohol. The preservatives should be selected having regard for the use of the composition and possible incompatibilities between the preservatives and other ingredients. Preservatives are employed in amounts ranging from about 0.01% to about 2% by weight of the composition. In a preferred embodiment, preservatives (antimicrobials) will be absent from the composition with the exception of pentylene glycol which has preservative activity.

Minor adjunct ingredients may also be included such as fragrances, antifoam agents, opacifiers and colorants, each in their effective amounts to accomplish their respective functions. Skin active materials may also be formulated with compositions of the present invention. These actives include retinoids such as retinol, retinyl palmitate and retinyl linoleate, alpha-hydroxycarboxylic acids, salicylic acid, potassium glycherrizinate, alpha-bisabolol and combinations thereof. Amounts of these materials may range anywhere from about 0.0001 to about 5% by weight.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLES 1–8

A series of cosmetic compositions typical of the present invention are reported in the Table below. These are gel emulsions.

TABLE I

| INGREDIENT | EXAMPLE (WEIGHT %) | | | | | | | |
|---|---|---|---|---|---|---|---|---|
| | 1 | 2 | 3 | 4 | 5 | 6 | 7 | 8 |
| PHASE A | | | | | | | | |
| Carbopol 1382 ® (2% Active in water) | 20.0 | 20.0 | 20.0 | 20.0 | 20.0 | 20.0 | 20.0 | 20.0 |
| Disodium EDTA | 0.1 | 0.1 | 0.1 | 0.1 | 0.1 | 0.1 | 0.1 | 0.1 |
| Butylene Glycol | 1.7 | 1.7 | 1.7 | 1.7 | 1.7 | 1.7 | 1.7 | 1.7 |
| Glycerin | 2.0 | 2.0 | 2.0 | 2.0 | 2.0 | 2.0 | 2.0 | 2.0 |
| Pentylene Glycol | 1.0 | 1.0 | 1.0 | 1.0 | 5.0 | 10.0 | 10.0 | 2.0 |
| Allantoin | 0.2 | 0.2 | 0.2 | 0.2 | 0.2 | 0.2 | 0.2 | 0.2 |
| Trehalose | 0.5 | 0.5 | 0.5 | 0.5 | 0.5 | 0.5 | 0.5 | 0.5 |
| Water | Bal. | Bal. | Bal. | Bal. | Bal. | Bal. | Bal. | Bal. |
| PHASE B | | | | | | | | |
| Herbal Extract | 1.0 | 1.0 | 1.0 | 1.0 | 1.0 | 1.0 | 1.0 | 1.0 |
| Borage Oil | 1.0 | 1.0 | 1.0 | 1.0 | 1.0 | 1.0 | 1.0 | 1.0 |
| Tridecyl Salicylate | 2.0 | 2.0 | 2.0 | 2.0 | 2.0 | 2.0 | 2.0 | 2.0 |
| Stearyl Alcohol | 1.3 | 1.3 | 1.3 | 1.3 | 1.3 | 1.3 | 1.3 | 1.3 |
| Sodium Cocoylisethionate | — | — | — | — | — | 3.0 | — | — |
| Sodium Lauryl Sulphate | — | — | — | — | — | — | 3.0 | — |
| Sodium Alkylamidopropyl betaine | — | — | — | — | — | — | — | 3.0 |
| Steareth-2 | 1.0 | 1.0 | 1.0 | 1.0 | 1.0 | 1.0 | 1.0 | 1.0 |
| Steareth-21 | 1.0 | 1.0 | 1.0 | 1.0 | 1.0 | 1.0 | 1.0 | 1.0 |
| Cetearyl Phosphate (Amphisol A ®) | 0.5 | 0.5 | 0.5 | 0.5 | 0.5 | — | — | — |
| Vitamin E Acetate | 0.5 | 0.5 | 0.5 | 0.5 | 0.5 | 0.5 | 0.5 | 0.5 |
| Phenonip ® | 0.4 | 0.4 | 0.4 | 0.4 | 0.4 | 0.4 | 0.4 | 0.4 |
| PHASE C | | | | | | | | |
| Silicone Copolyol (EM-97) | 1.0 | 1.0 | 1.0 | 1.0 | 1.0 | 1.0 | 1.0 | 1.0 |
| Cyclomethicone (DC 345 ®) | 3.0 | 3.0 | 3.0 | 3.0 | 3.0 | 3.0 | 3.0 | 3.0 |
| Silicone Elastomer Mixture (35% Elastomer Solids in Cyclomethicone) | 35.0 | 30.0 | 25.0 | 20.0 | 10.0 | 5.0 | 55.0 | 35.0 |
| Fragrance | 0.15 | 0.15 | 0.15 | 0.15 | 0.15 | 0.15 | 0.15 | 0.15 |
| PHASE D | | | | | | | | |
| Water | 2.0 | 2.0 | 2.0 | 2.0 | 2.0 | 2.0 | 2.0 | 2.0 |
| Potassium Hydroxide Solution (45% Active) | 0.7 | 0.7 | 0.7 | 0.7 | 0.7 | 0.7 | 0.7 | 0.7 |
| DL-Panthenol | 0.2 | 0.2 | 0.2 | 0.2 | 0.2 | 0.2 | 0.2 | 0.2 |
| PHASE E | | | | | | | | |
| Algae Extract | 1.0 | 1.0 | 1.0 | 1.0 | 1.0 | 1.0 | 1.0 | 1.0 |
| Gorgonian Extract | 1.0 | 2.0 | 3.0 | 0.01 | 0.10 | 1.0 | 1.0 | 1.0 |
| Water | 5.0 | 5.0 | 5.0 | 5.0 | 5.0 | 5.0 | 5.0 | 5.0 |

EXAMPLE 9

A clinical study was performed on a base composition similar to the base composition in Example 1.

The base formula included polysiloxane elastomer as well as an irritating anionic surfactant, cetearyl phosphate (available as Amphisol®). The base was compared with an identical formulation that further contained 0.25% gorgonian extract (in butylene glycol).

The clinical study involved applying the control base formula to one arm and the gorgonian extract containing formula to the other. Test sites were dosed with 2 mg per cm². Test materials remained on the skin for 30 minutes, at which time a chromameter reading (L*a*b* values) were taken and the change from zero time in a* values were calculated.

The average change in a* for the base and base/gorgonian extract were respectively 2.06 and 1.60. It is evident that the gorgonian extract had a significant influence on reducing the redness of irritation over the applied area. Significance of the results were evaluated by t-test statistical analysis. The base and base/gorgonian extract respectively had a t-test error of 0.05 and 0.45.

The foregoing description and examples illustrate selected embodiments of the present invention. In light thereof variations and modifications will be suggested to one skilled in the art, all of which are within the spirit and purview of this invention.

What is claimed is:

1. A cosmetic composition comprising:
   (i) from about 0.1 to about 35% by weight of a surfactant;
   (ii) from about 0.00001 to about 3% by weight of gorgonian extract;
   (iii) from about 0.01 to about 30% by weight of a cross-linked non-emulsifying siloxane elastomer; and
   (iv) a pharmaceutically acceptable carrier to deliver the surfactant and extract.

2. A composition according to claim 1 which is an emulsion of the water-in-oil type.

3. The composition according to claim 1 wherein the surfactant comprises an anionic surfactant.

4. The composition according to claim 3 wherein the anionic surfactant is a $C_8$–$C_{20}$ alkyl phosphate salt.

5. The composition according to claim 1 wherein the elastomer is dimethicone/vinyl dimethicone cross polymer.

* * * * *